(12) United States Patent
Dorfmann et al.

(10) Patent No.: US 8,766,819 B2
(45) Date of Patent: Jul. 1, 2014

(54) CREW ALLERTNESS MONITORING OF BIOWAVES

(75) Inventors: Cindy Dorfmann, Darmstadt (DE); Andre Lutz, Darmstadt (DE)

(73) Assignee: The Boeing Company, Chicago, IL (US)

( * ) Notice: Subject to any disclaimer, the term of this patent is extended or adjusted under 35 U.S.C. 154(b) by 122 days.

(21) Appl. No.: 13/162,854

(22) Filed: Jun. 17, 2011

(65) Prior Publication Data
US 2012/0319869 A1    Dec. 20, 2012

(51) Int. Cl.
*G08B 21/00*    (2006.01)
(52) U.S. Cl.
USPC ......... 340/945; 340/980; 340/573.1; 340/971
(58) Field of Classification Search
USPC .............. 340/945, 573.1, 980, 974, 975, 971, 340/965; 701/3, 36, 14; 600/509, 301, 382, 600/372, 547
See application file for complete search history.

(56) References Cited

U.S. PATENT DOCUMENTS

| | | | |
|---|---|---|---|
| 5,353,071 A | | 10/1994 | Bradshaw |
| 6,567,014 B1* | | 5/2003 | Hansen et al. ................. 340/980 |
| 2004/0002638 A1 | | 1/2004 | Yanagidaira et al. |
| 2006/0220883 A1* | | 10/2006 | Matos ......................... 340/573.1 |
| 2008/0177197 A1* | | 7/2008 | Lee et al. ..................... 600/545 |
| 2009/0024260 A1* | | 1/2009 | Deleris et al. .................. 701/14 |
| 2009/0171232 A1 | | 7/2009 | Hu et al. |
| 2010/0033333 A1* | | 2/2010 | Victor et al. .................. 340/576 |
| 2010/0049066 A1* | | 2/2010 | Hatakeyama ................. 600/509 |
| 2012/0078445 A1* | | 3/2012 | Krupansky et al. ............... 701/3 |
| 2012/0215403 A1* | | 8/2012 | Tengler et al. .................. 701/36 |

FOREIGN PATENT DOCUMENTS

| | | |
|---|---|---|
| EP | 0545497 A1 | 6/1993 |
| GB | 2343954 A | 5/2000 |
| JP | 2009022370 A1 | 2/2009 |

OTHER PUBLICATIONS

Jones, Willie D., Taking Body Temperature, Inside Out, IEEE Spectrum, Jan. 2006.
Kircher, A., Uddman, M., Sandin, J., Vehicle control and drowsiness, VTI Meddelande 922A, 2002.
Chin-Teng Lin Che-Jui Chang Bor-Shyh Lin Shao-Hang Hung Chih-Feng Chao I-Jan Wang, A Real-Time Wireless Brain—Computer Interface System for Drowsiness Detection, IEEE Transactions onBiomedical Circuits and Systems, vol. 4, issue 4, pp. 214-222, Aug. 2010.
Sucholeiki, Roy, MD, Normal EEG Waveforms, eMedicine Medscape reference, Aug. 13, 2010 downloaded from http://emedicine.medscape.com/article/1139332—overview.
Secarea, Jr., V.V., "Beyond Knobs and Dials: Toward an Intentional Model of Man-Machine Interaction"; IEEE, 1990.

\* cited by examiner

*Primary Examiner* — Hoi Lau
(74) *Attorney, Agent, or Firm* — Felix L. Fischer (57) ABSTRACT

A system for display management based on operator stress level employs a biosensor detecting stress level of an operator. A biomonitoring system receives input from the biosensor and provides an output responsive to a threshold of stress. An operational display control receives the output from the biomonitoring system and modifies an information display based on the stress threshold.

8 Claims, 7 Drawing Sheets

CREW ALLERTNESS MONITORING OF BIOWAVES

BACKGROUND INFORMATION

1. Field

Embodiments of the disclosure relate generally to the field of operator mental state monitoring and more particularly provides a system and method for monitoring alertness of an operator such as a pilot for lowered alertness and high stress states with alertness recovery stimulation, normal display functionality and reduced display clutter based on thresholds for accommodation of the mental state of an operator,

2. Background

Operators of modern vehicles and machinery, particularly pilots of aircraft, are provided with significant information by instruments and systems displays in the vehicle or machine being operated. Often the amount of data presented on system displays can be very complex. Operators, particularly pilots, also may be required to remain in control of the vehicle for significant periods of time. Additionally, increasingly high stress levels may be induced by traffic congestion, bad or, severe weather, aircraft damage or other emergencies, or combat situations. The mental state or condition of the operator affects how well the operator can assimilate information presented by the instruments and systems displays.

It is therefore desirable to provide a system and method for monitoring alertness of an operator such as a pilot for lowered alertness and high stress states with control system adjustment for accommodation of the mental state.

SUMMARY

Embodiments described herein provide a system for display management based on operator stress level which employs a biosensor detecting stress level of an operator. A biomonitoring system receives input from the biosensor and provides an output responsive to a threshold of stress. An operational display control receives the output from the biomonitoring system and using software modules modifies an information display based on the stress threshold.

In an exemplary embodiment. An aircraft cockpit display management system responsive to pilot stress level incorporates a biomonitoring sensor package including sensors selected from the set of a neuro-headset to read the brainwaves, sensors to read to heart rate, temperature, perspiration level, respiration and eye movement sensing. A biomonitoring system receiving input from the biomonitoring sensor package provides an output responsive to a threshold of stress. An operational display control receives the output from the biomonitoring system and using software modules modifies an information display for decluttering based on a predetermined elevated stress threshold.

In one operational scenario, the exemplary embodiment provides a method for display management based on operator stress level which initializes an operational display control with base values for display complexity and then monitors output of a biosensor. A current stress value is calculated based on the biosensor output to determine if a lower initial threshold has been exceeded indicating reduced attentiveness. If so, a display management system is notified that a first lower threshold has been exceeded and activates additional tasks to raise the operator's alertness level. A determination is made if normal stress levels have returned and, if so, to normal operational display complexity is restored, The features, functions, and advantages that have been discussed can be achieved independently in various embodiments of the present invention or may be combined in yet other embodiments farther details of which can be seen with reference to the following description and drawings,

DETAILED DESCRIPTION

Figure 1:
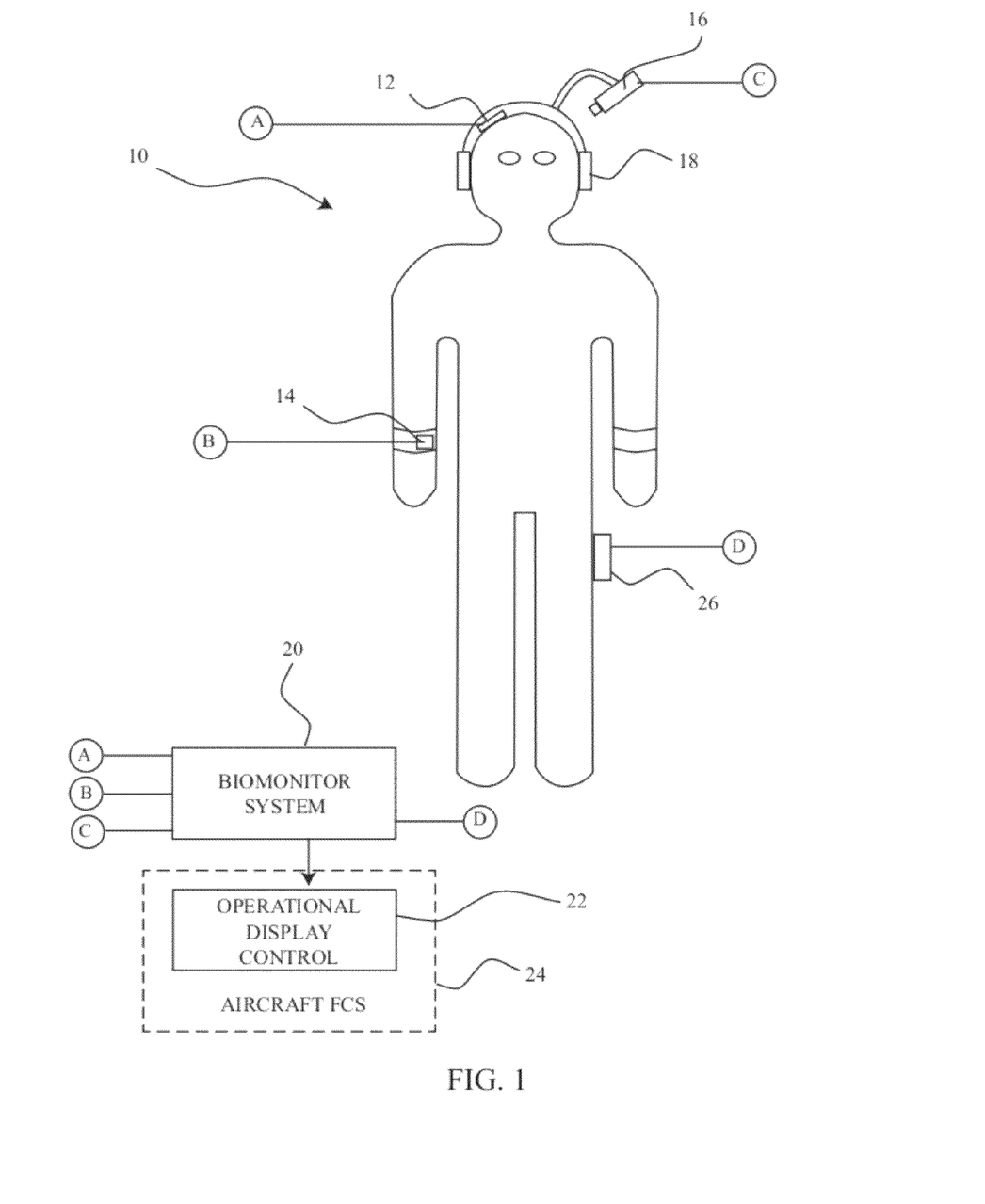
FIG. 1 is a schematic block diagram of the bio-monitoring system sensors and control.

The embodiments described herein relate to an aircraft system with a pilot. However, the described system and method are equally applicable to operators of heavy machinery, ships, military vehicles or other devices both mobile and stationary and the term operator is used as a general descriptor herein. The example embodiment provides a biomonitoring sensor package 10 attached to the operator incorporating sensors as shown in FIG. 1 including a neura-headset 12 to read the brainwaves, cuff mounted sensors 14 to read to heart rate and other biosignals such as temperature or perspiration level, and a visual sensing device such as :video camera 16 for monitoring eye movement. The video camera may be mounted to a headset 18 or helmet as shown in FIG. 1 or to a remote support on the instrument panel or cockpit structure. The biomonitoring sensor package 10 provides signals to a biomonitor system 20 through either wired or wireless communications interfaces (designated. B and C) and constantly monitors the mental state of the operator by reading the signals and comparing them to one or more predefined thresholds. As will be described in greater detail subsequently, more than one threshold may be present to grade the system reaction to operator mental state or behavior.

Figure 2A:
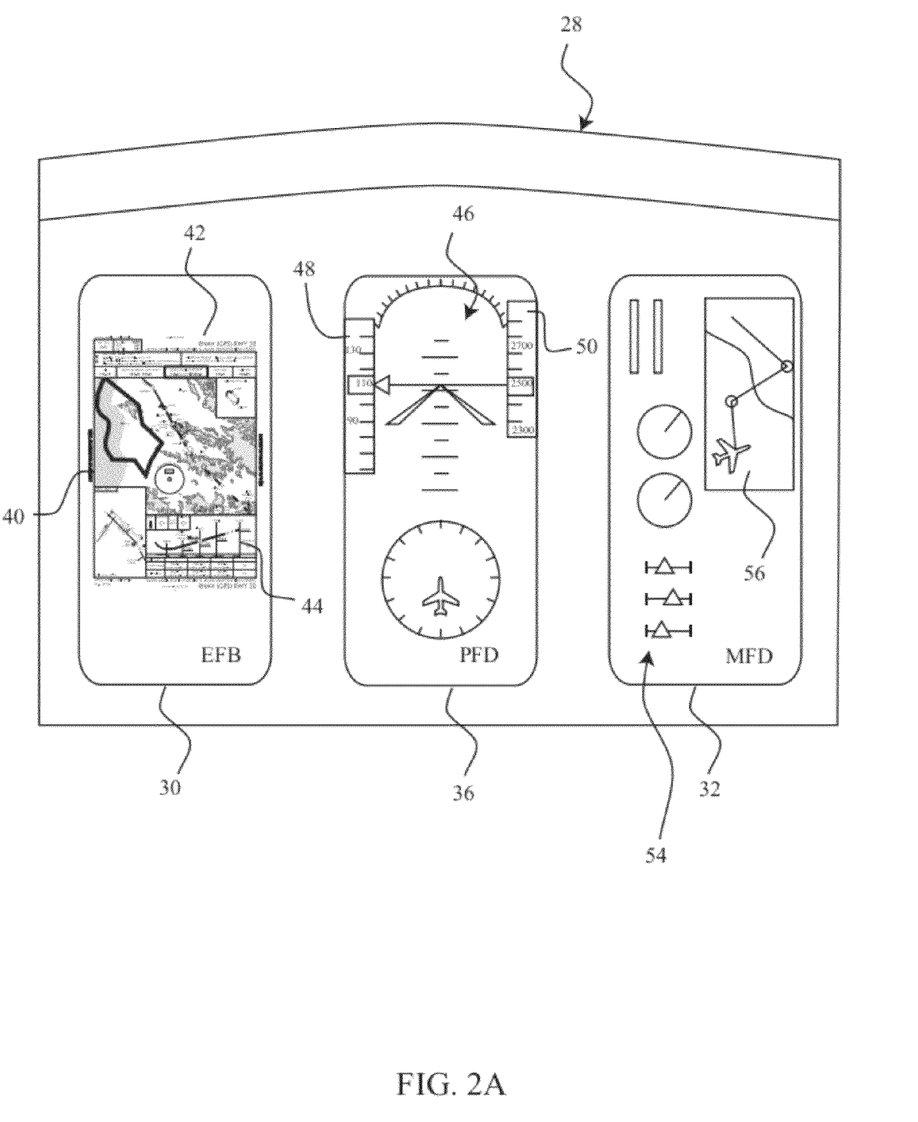
FIG. 2A is a simulated view of a cockpit display system for normal conditions.

If a threshold is reached or is approached, a message is sent by the biomonitoring system 20 to an operational display control 22, integrated into the computer system for the aircraft flight control system 24, which includes the displays in the cockpit 28 and controls such elements as the Electronic Flight Bag (EFB) 30, Primary Flight Display (PM) 32 and/or Multifunction Display (MFD) 36 (sometimes referred to as a Navigational Display (ND) when employed for that function) shown in FIG. 2A. Examples of normal cockpit display details on the EFB, PFD and MFD/ND displays in the cockpit are represented in FIG. 2A. The EFB will typically display navigational information such as course maps 40, destination airport information or Notices to Airmen (NOTAMS) 42 and vertical flight path information 44. The PFD 36 will display vertical position indication/turn and bank information 46, airspeed, 48, altitude 50 and horizontal direction indication 52. The MFD 32 typically displays aircraft system information 54 and flight path information 56

Figure 2B:
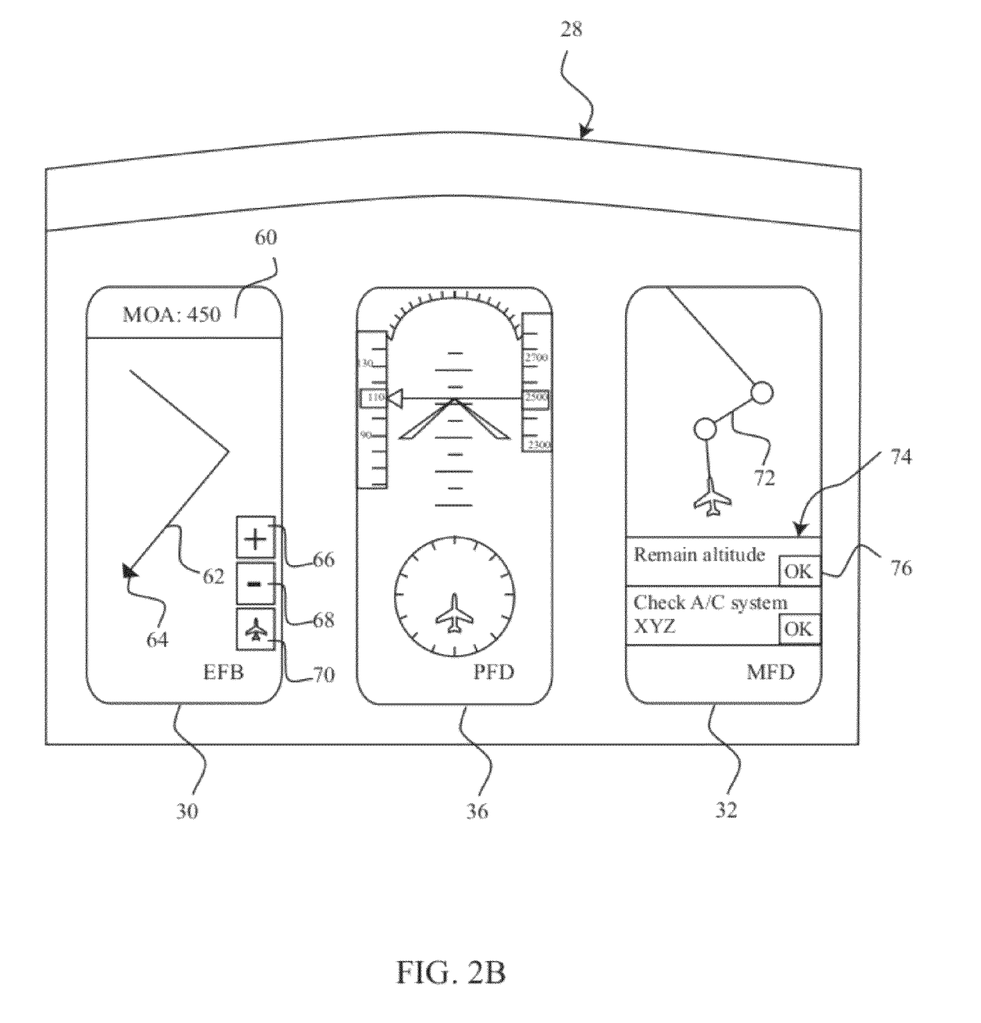
FIG. 2B is a simulated view of the cockpit display system after adjustment for a first threshold based on mental state.
Figure 2C:
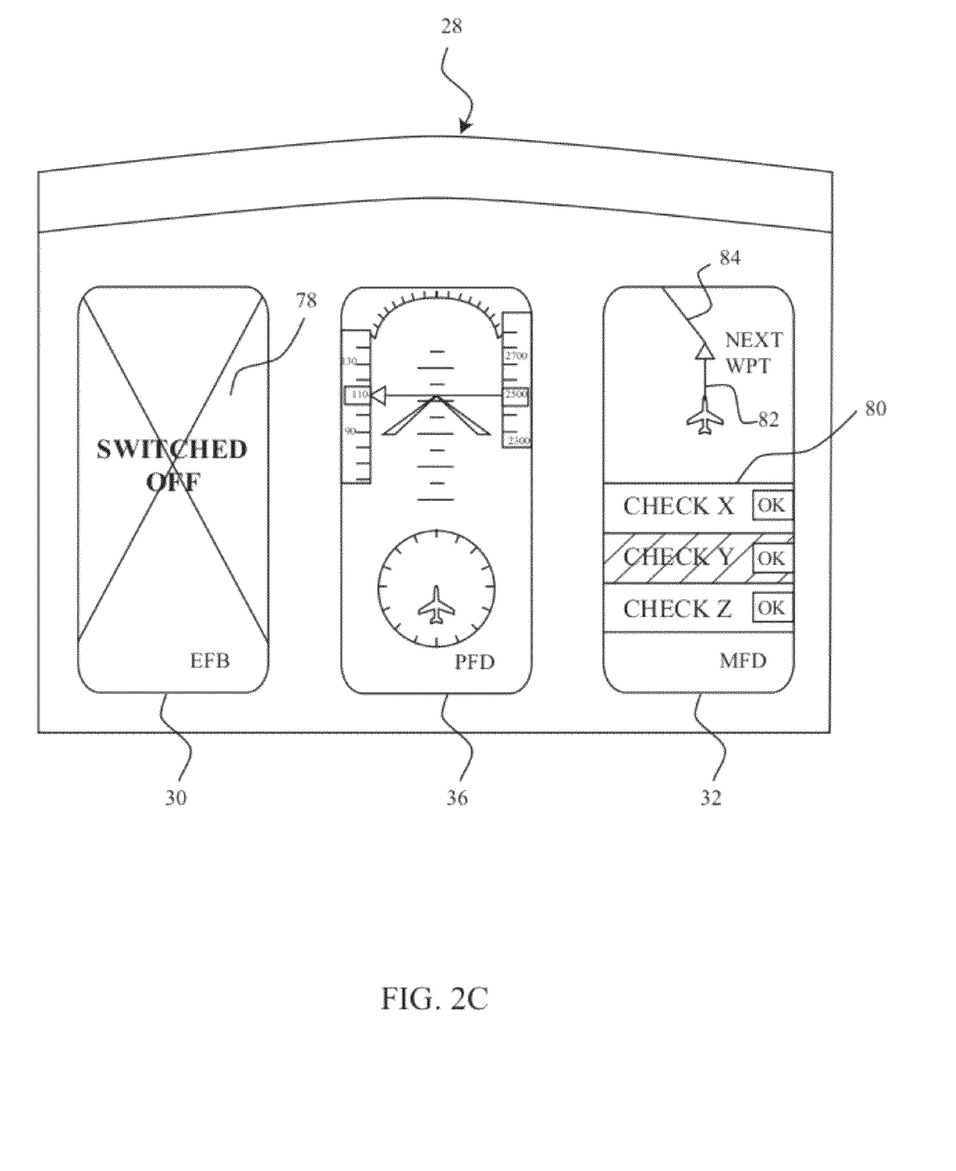
FIG. 2C is a simulated view of the cockpit display system after adjustment for a second threshold based on mental state; and, FIG. 3 is a flow chart of a calibration method to establish database values for reduced alertness thresholds.

The operational display control 22 in the FCS 24 is computer controlled and incorporates software modules providing different modes responsive to signaling from the biomonitor system 20. One mode is "biosignal threshold reached". If this mode is activated, the operational display control 22 will automatically declutter the screen displays dramatically and focus only on the information the operator needs right now to fly the aircraft (e.g. turn off NOTAM depiction on the EFB 30). Levels of display decluttering are shown in FIGS. 2B and 2C which will be described in greater detail subsequently. In a combined cockpit computer system, some displays are switched off automatically to control the operator's attention and draw it to the system(s) that need his intention most at that particular moment. The biomonitoring system 20 will continue reading the biosignals of the operator. The operational display control 22 would then revert into "normal" mode when biosignals return to "normal" within the threshold limits. Alternatively, an override or reset switch associated with the operational display control 22 may be employed to restore complete normal functionality to the displays.

The monitoring devices including the sensors of the biomonitoring sensor package 10 and the associated biomonitor system 20 is a personal device and therefore is configured to the person wearing it. Calibration of the combined biomonitoring sensor package and biomonitor system may be undertaken for specifically "tuning" defined threshold levels for individuals. The biomonitoring sensor package 10 and associated biomonitor system 20 would also be able to detect any emotional stress (e.g. problems the operator has at home or other personal issues) and may automatically change the depiction,/ arrangement of displays and application presented by the operational display control 24 as soon as it is switched on. There could be a color adjustment of the EFB application, of course the color adjustment would not affect any critical elements but, for example, the main background color or the frame of the application or buttons could change color to bring the operator into a less emotional mood (e.g. blue color or grey color could have a calming/neutralizing effect). It would therefore be independent of "emergency-only" situations The neuro-headset 12 of biomonitoring sensor package 10 monitors electroencephalogram (EEG) signals of the operator. The brain waves need to be captured as close to the skull as possible. The operator is typically wearing a headset 18 or helmet while flying the aircraft. A sensor is attached to the headset that can then directly read the brain waves from the operator's skull. The EEG is the depiction of the electrical activity occurring at the surface of the brain and is a primary method used to detect wake conditions and stress state of the operator. Normal EEG waveforms, like many kinds of waveforms, are defined and described by their frequency, amplitude, and location. For example, rising alpha (8-11 Hz) and theta (4-7 Hz) EEG activities indicate loss of attentiveness or alertness and thus the potential for lapses in attention and behavior. The main indicator of stress is beta brain waves above 18 Hz. With that level the operator feels slightly stressed due to having to perform several tasks at the same time. When the brainwave level increases above 30 Hz the brainwaves will interfere with the ability to think clearly and effectively which becomes a threat to the operators and aircrafts safety. The operator feels confused and will not be able to focus on one task. This would be the indicator for a very high stress level like maybe in an emergency situation (in case of multiple engine failures etc.) The biomonitor system 20 employs Alpha and Theta waves to define the condition of the operator (e.g. sleepy, stressed).

The biomonitor system 20 verifies the detected state/ condition of the operator with a combination of two or more measurement methods. The heart rate, body temperature or muscle active measurement requires additional sensors or electrodes attached to the skin of the operator. This can be resolved by sewing the sensor into the operator's uniform (e.g. at a position at the sleeves of a shirt close to the wrist) where it contacts the skin. The secondary source of bio data measurements for the example embodiment is provided by the cuff mounted sensor 14 for heart rate variability, body temperature or muscle activity. This enables a second reading of measurement that can be matched to the brain wave reading, As an additional measurement eye movement is employed. The slower the eye movement the more likely the operator has a reduced alertness. This can result in less attention on the task and can be measured in blink duration and blink frequency. Video camera 16 is installed in the cockpit to be able to record the eye movement of the operator as well as blink duration and frequency. Software modules in the biomonitor system 20 are then used to automatically evaluate and interpret the measurement and then match it to the brain wave reading. Alternative measurable inputs such as respiration rate may also or alternatively be employed.

From the combination of two sensor inputs (primary: Brain wave reading via headset, secondary: heart rate reading via sensor in operators uniform) bio-monitoring data can be extracted. This data is compared to an average value of this operator in a neutral state (awake, not stressed or tired). Comparing the measurements to the average value the software modules in the biomonitor system 20 can detect any deviation from a predetermined buffer area around the average. In case of an abnormal comparison result several actions are possible depending on the direction of the reading (towards reduced alertness, towards highly stressed).

In case of reduced alertness detection the reaction of the cockpit system can also vary depending on the "severity" of alertness reduction. If the biomonitor system 20 detects that the operator reaches an initial reduced alertnesse threshold, additional distraction/more tasks to be fulfilled are provided by the operational display control 22. If the biomonitor system 20 detects that the operator reaches a second reduced alertness threshold an output signal (represented as D in FIG. 1) may activate a vibration module 26 in the seat of the operator in order to increase alertness of the operator. Alternatively, aural or visual indicators can be presented by the operational display control 22.

In case of an increased stress detection by the biomonitor system 20 the operational display control can automatically start to declutter various screens on the front panel to reduce information and distraction. In case of emergency or other stressful situations the operational display control can automatically display a priority list of tasks. Instead of blinking and voice commands of various systems (in case of a multi system failure) the system will detect the stress level of the operator and then adapt the warning messages and methods. It can, for example, focus the operator's attention on the task with a predetermined highest priority, On a data driven charting EFB 30, all unimportant data for the current situation can be decluttered/reduced when a high work load/stress level is detected, e.g. radio frequencies, all shown waypoints reduced to next waypoint, airspace depictions reduced to important airspaces in vicinity such as nearest airport for landing.

On MFD 32 an appropriate checklist can be shown, for example if there are several warnings in the cockpit an optimized checklist is provided to the operator for the next tasks to help him to work on the tasks in a prioritized order. Dependant on the number of stress level thresholds, an appropriate depiction for each level is chosen for each display for each phase of flight. The decluttering differs for the various phases of flight. For the different warnings in the aircraft, the aircraft manufacturer determines in which order the response checklists are depicted.

FIG. 2B shows an example of a first level of "decluttering" in response to exceeding the initial upper threshold for stress. In the EFB 30 the operational display control enlarges the most important elements (like text information that can be easily missed such as Minimum Operating Altitude (MOA) display 60) and positions them more prominent in the primary field of view. The number of displayed map elements is reduced, for example only displaying route 62 and associated waypoints 64, no additional text, with only main functions like "zoom in" 66, "zoom out" 68, "center on A/C" 70 available for selection.

On the PFD no changes are made and the PFD creates a "fall back" solution; one system should always look the same and contain the most basic instruments/panels.

With respect to the MFD/ND, the display is decluttered for example only depicting immediately required information (e.g. current route 72). If an emergency or failure is detected in the system, a checklist 74 can be displayed. The operator is forced to elect check off boxes 76 (to assure that required checks are performed).

FIG. 2C demonstrates the additional decluttering created upon exceeding the secondary threshold. In stress level 2, the EFB 30 may be switched off by the biomonitoring system, dependant on the flight phase. An indicator 78 is provided to show that the system was switched off on purpose, not due to power loss. A function to return to the last displayed screen, "one click" functions to access information for "nearest airport", "go around procedure chart", etc. may be alternatively provided. In case of a system failure the operator needs to focus on controlling the aircraft and on checklists.

As with stress level 1 previously described, the PFD 36 remains unchanged.

The MFD 32 can be used to depict a checklist 80 comparable to that provided for stress level I but with enhanced sizing or color features, the example includes a miniature depiction of the current flight plan 82 (including current position and the next waypoint 84 only) as well as the checklist. Checklist items for Captain and First Officer may be separated. Here in shown as "clear" items for CPT, "shaded" items to be checked by the FO, text/font size is enlarged the better readability with the "OK" buttons 86 to confirm check of the item.

Figure 3:
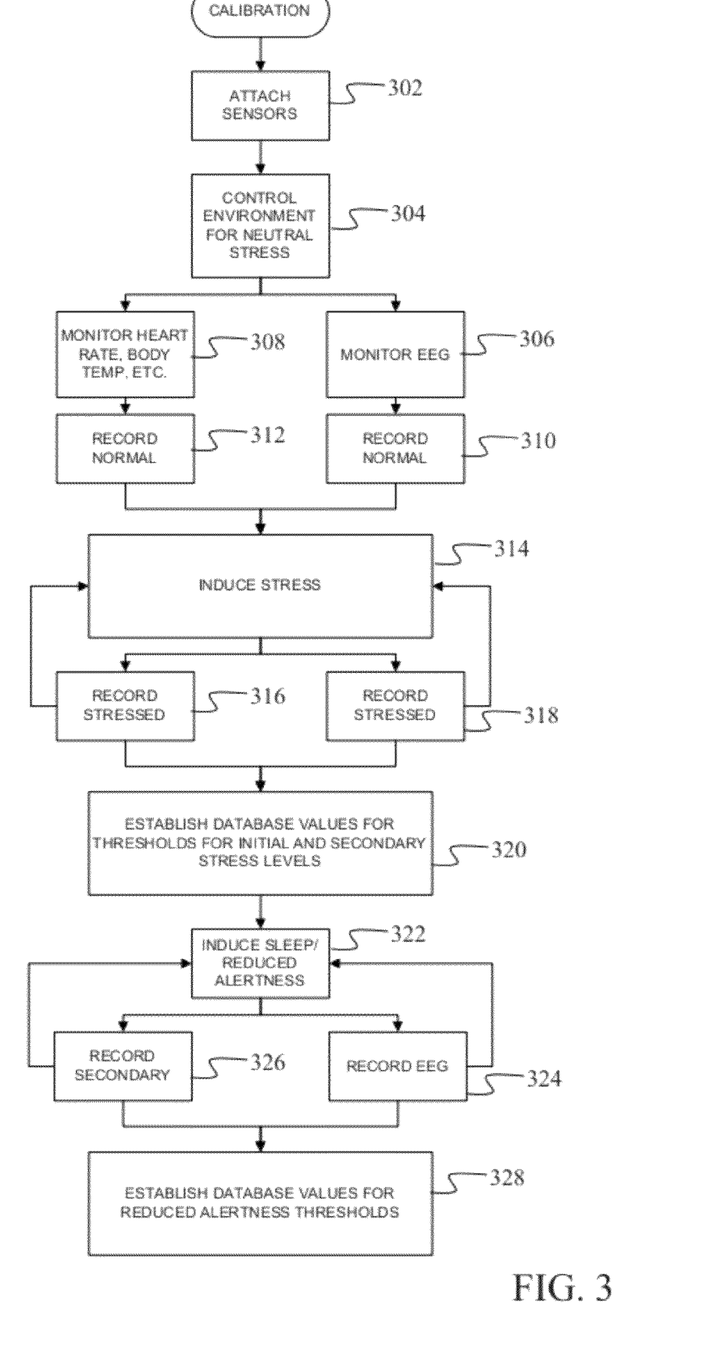
Figure 4A:
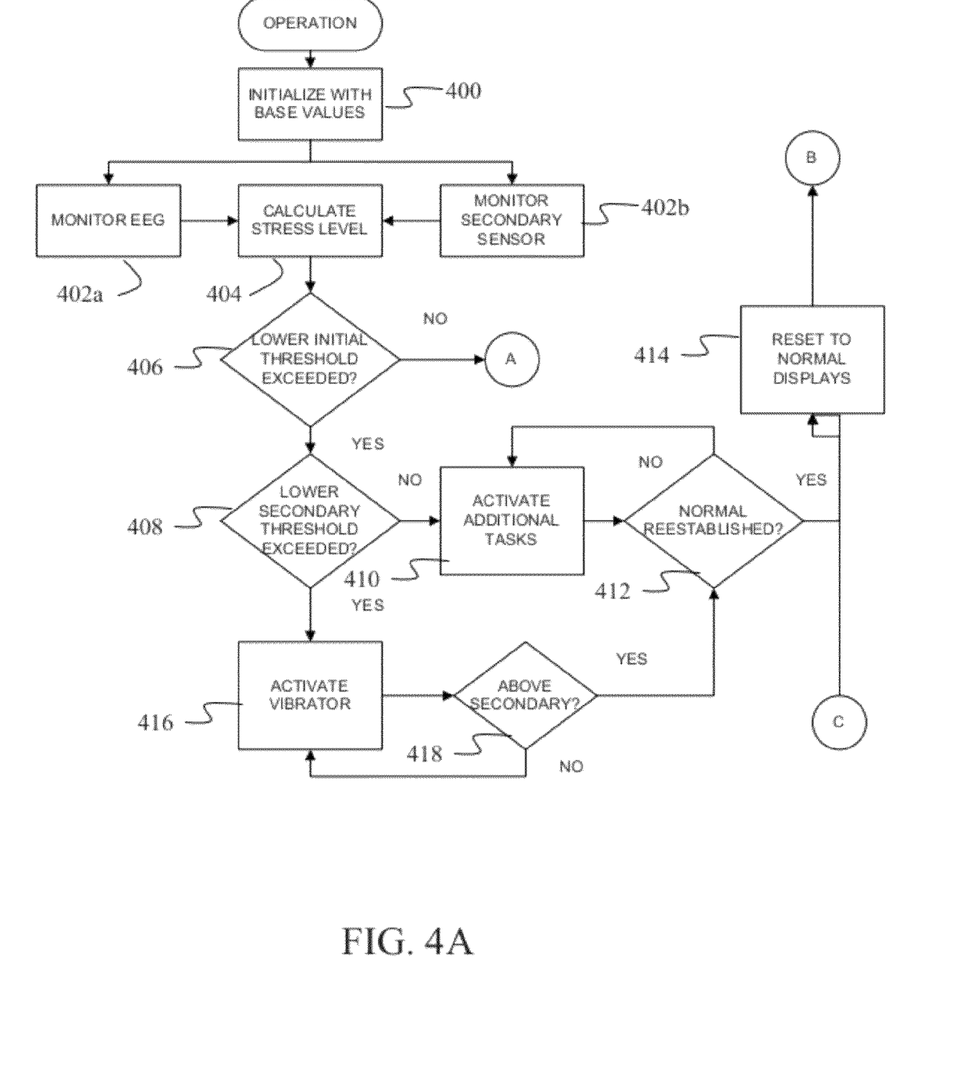
FIGS. 4A and 4B are a flow chart of operation of the system
Figure 4B:
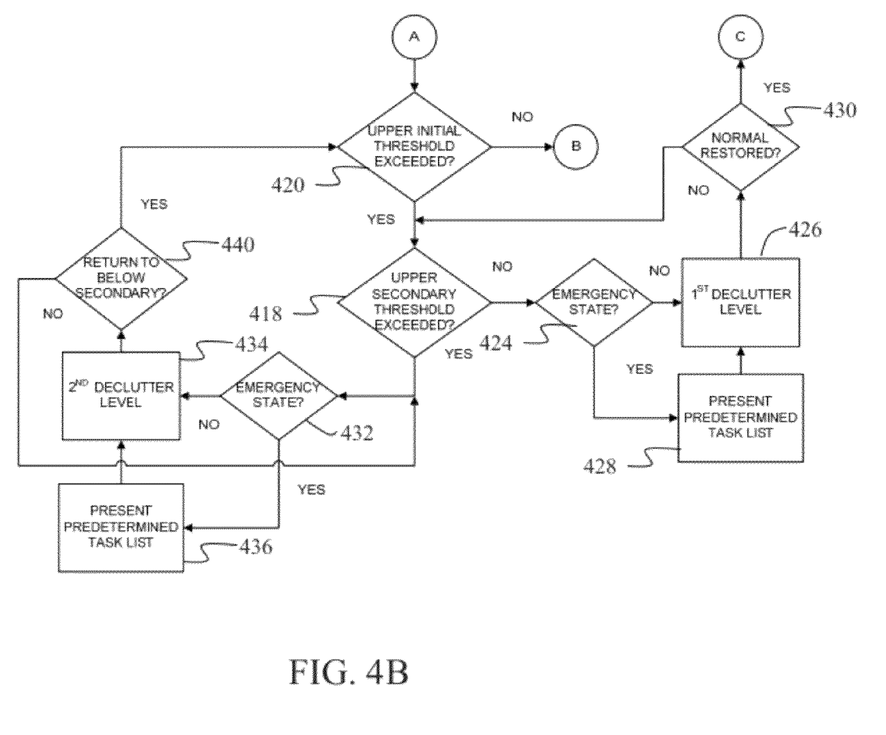

The EFB and/or MFD may alternatively each be used to display a checklist (e.g. having one checklist for the pilot and one for the FO displayed), FIGS. 3, 4A and 4B depict a method employing the embodiments described or implementing an interactive display control system based on operator stress level. Calibration of the overall system is accomplished as shown in FIG. 3. The sensors in the biosensor monitoring package are attached to the operator, step 302, for the embodiment disclosed by donning a flight suit or uniform shirt with the cuff mounted sensor and headset with the EEG sensor. A controlled environment is established with the operator in a well rested state in a simulator of the cockpit or similar device, step 304. The biomonitor system then monitors EEG, step 306, heart rate and body temperature, step 308, from the biosensor monitoring package and after an equalization period a normal stat is recorded for EEG, step 310 and heart rate/body temperature, step 312. Stress is then induced on the operator by simulated emergencies in the simulator or other stress inducer, step 314 and the resulting EEG is measured, step 316, and heart rate/body temperature is measured, step 318. This may be repeated a number of times for data confirmation and/or at varying stress levels to obtain extended data points. One or more threshold levels are then established from the data, step 320. A sleep state is then induced in the operator (this may occur in a separate environment at a selected time for normal sleep), step 322. The resulting EEG is measured, step 324, and heartrate/body temperature is measured, step 326. Data may be recorded over a period of time for wakefulness to sleep transition values. One or more threshold levels are then established from the data for reduced alertness, step 328.

FIGS. 4A and 4B demonstrate the method for operational implementation of the system based on the calibration data. Upon entry into the cockpit by the operator, the biomonitoring sensor package 10 is connected to the biomonitor system 20 and the operational display control 22 is initialized with base values for display complexity, step 400. The biomonitor system 20 then monitors EEG from the headset sensor 12 and secondary sensors from the cuff sensor 14, steps 402a and 402b. The biomonitor system then calculates a current stress value based on the sensor inputs, step 404. A determination is made if a lower initial threshold has been exceeded indicating operator reduced attentiveness, step 406. If not, the monitoring system tests for higher stress level thresholds as will be described in greater detail subsequently. If the lower initial threshold has been exceeded, the system determines if the operator has, in fact, passed a sleep threshold, step 408. If not, the operational display control 22 is notified that the drowsiness threshold has been exceeded and additional tasks are activated, step 410, to raise the operator's alertness level. Repeated biosensor system monitoring is employed to determine if normal stress levels have returned, step 412. If not, the additional tasks presentations by the operational display control 22 are continued and or varied in a predetermined manner. If normal conditions have returned, the biomonitor system 20 indicates a normal stress level and the operational display control 22 is reset to normal operational display complexity 414.

If in step 408 a determination was made that the sleep threshold had been reached, the biomonitor system 20 activates the vibrator 26 and/or other aural or physical stimulus to wake up the operator, step 416. If wakefulness is achieved, step 418, the system returns to step 412 to determine if normal stress levels are present or whether additional tasks to further stimulate the operator are required.

If the biomonitor system determined in step 406 that no drowsiness was present then testing for elevated stress levels is made and a determination if an initial upper threshold for stress has been exceeded, step 420. If not, monitoring continues with a return to node B. If the initial threshold has been exceeded, a determination is made if a second upper threshold level has been exceeded, step 422, if not, a determination is made if an emergency state exists which is causing the increased stress level, step 424. If not, the biomonitor system instructs the operational display control system 22 and a first declutter level is established, step 426. If an emergency state exists in step 424 the operational display control 22 provide a predetermined display of prioritized tasks to address the emergency, step 428 and then the first declutter level on the displays is established, step 426. The system then monitors the sensor levels and if normal stress levels return, step 430, the system returns through node C for resetting the normal display levels.

If the second upper threshold level has been exceeded in step 422, a determination is made if an emergency state exists which is causing the increased stress level, step 432. If not, the biomonitor system instructs the operational display control system 22 and a second declutter level is established, step 434. If an emergency state exists in step 432 the operational display control 22 provides a predetermined display of prioritized tasks to address the emergency, step 436, which is further edited consistent with the second level threshold of increased stress and then the second declutter level on the displays is established. Monitoring of sensor levels then continues to determine if the stress level has dropped below the second upper threshold, step 440. If so, the system returns to step 420 for the initial upper threshold level determination with the associated first declutter levels and task lists, if required, and, if stress levels return to normal, a reset of the system for normal operation.

Having now described various embodiments of the invention in detail as required by the patent statutes, those skilled in the art will recognize modifications and substitutions to the specific embodiments disclosed, herein. Such modifications are within the scope and intent of the present invention as defined in the following claims.

What is claimed is:

1. A method for display management based on operator stress level comprising:
    initializing an operational display control with base values for display complexity;
    monitoring output of a biosensor;
    calculating a current stress value based on the biosensor output determining if a lower initial threshold has been exceeded indicating reduced attentiveness;
    if so, notifying that the lower initial threshold has been exceeded and activating additional tasks to raise the operator's alertness level;
    determining if normal stress levels have returned;
    if so, reseting to normal operational display complexity;
    determining if a lower secondary threshold had been reached;
    if so, activating a vibrator and/or other aural or physical stimulus to increase operator alertness;
    if alertness above the lower secondary threshold is achieved, determining if normal stress levels are present or whether additional tasks to further stimulate the operator are required.

2. The method as defined in claim 1 further comprising:
    a determining if an initial upper threshold for stress has been exceeded; if
    so, decluttering the display.

3. The method as defined in claim 2 further comprising;
    determining if an emergency state exists which is causing the increased stress level;
    if so, providing a predetermined display of prioritized tasks to address the emergency.

4. The method as defined in claim 2 further comprising:
    determining if stress has been reduced below the initial upper threshold;
    if so, returning the display to normal complexity.

5. The method as defined in claim 2 further comprising:
    determining is a second upper threshold level has been exceeded;
    if so, decluttering the display to a second level.

6. The method as defined in claim 5 further comprising:
    determining if an emergency state exists;
    if so, providing a predetermined display of prioritized tasks to address the emergency.

7. The method as defined in claim 1 wherein the step of monitoring output of a biosensor comprises monitoring EEG from a headset sensor.

8. The method as defined in claim 7 further comprising monitoring secondary sensors selected from the set of heart rate, temperature, perspiration level, respiration and eye movement.

* * * * *